（12) United States Patent
Okada et al.

(10) Patent No.: US 6,534,305 B2
(45) Date of Patent: Mar. 18, 2003

(54) PROCESS FOR AEROBIC CULTURE USING SINTERED METAL MEMBRANE

(75) Inventors: Atsushi Okada, Kanagawa (JP); Yoshitaka Teratani, Kanagawa (JP); Naohiro Kadota, Kanagawa (JP); Hisao Itou, Kanagawa (JP); Kazuhiro Satou, Kanagawa (JP)

(73) Assignee: Ajinomoto Co., Inc., Tokyo (JP)

( * ) Notice: Subject to any disclaimer, the term of this patent is extended or adjusted under 35 U.S.C. 154(b) by 0 days.

(21) Appl. No.: 10/023,709

(22) Filed: Dec. 21, 2001

(65) Prior Publication Data
US 2002/0123125 A1 Sep. 5, 2002

(30) Foreign Application Priority Data
Dec. 26, 2000 (JP) .......................................... 2000-396200

(51) Int. Cl.$^7$ ................................................. C12N 5/02
(52) U.S. Cl. ................. 435/256.8; 435/243; 435/254.1; 435/206.6; 435/325; 435/410

(58) Field of Search ............................... 435/243, 254.1, 435/256.8, 286.6, 410, 325

(56) References Cited
U.S. PATENT DOCUMENTS 3,984,286 A * 10/1976 Malick
4,693,827 A * 9/1987 Mordorski
5,705,072 A * 1/1998 Haase
6,069,009 A * 5/2000 Pepin et al.

\* cited by examiner

*Primary Examiner*—Leon B. Lankford, Jr.
(74) *Attorney, Agent, or Firm*—Oblon, Spivak, McClelland, Maier & Neustadt, P.C.

(57) ABSTRACT

A process for aerobic culture in which ammonia and oxygen are simultaneously supplied, comprising: dispersing and supplying air, oxygen, or a mixed gas thereof into a culture tank through a sintered metal membrane attached the end of a diffusing pipe, and simultaneously, dispersing and supplying ammonia or a mixed gas of ammonia and air into the culture tank through a diffusing pipe other than the above diffusing pipe.

2 Claims, 2 Drawing Sheets

PROCESS FOR AEROBIC CULTURE USING SINTERED METAL MEMBRANE

BACKGROUND OF THE INVENTION

1. Field of the Invention

The present invention relates to a method for improving productivity of aerobic culture by supplying oxygen using a sintered metal membrane in aerobic fermentation of useful substances.

2. Background Art Relating to the Invention

In fermentation industry, aerobic culture has been frequently conducted, wherein oxygen is supplied by aeration with stirring. In a conventional culture tank, oxygen is supplied to fungus bodies by aeration with stirring wherein air supplied from an aeration line equipped in the culture tank is finely dispersed by stirring blades. In this process, however, a problem of insufficient oxygen supply arises when oxygen consumption by fungus bodies is large due to a high fungus body concentration or a high production rate of a useful substance by the fungus bodies.

Thus, in order to improve oxygen supply to a culture liquid, use of oxygen instead of air as the supplying gas has been examined. However, there are problems that facilities for generating oxygen and maintenance thereof are required and a gas having a high oxygen concentration relative to air is discharged because sufficient oxygen supply is impossible by the conventional aeration with stirring even when oxygen is supplied.

Moreover, for the purpose of finely dispersing supplied air in an aerating stirrier, oxygen-supplying ability can be improved by increasing power for stirring. In this case, however, cavitation occurs when power for stirring is increased beyond a limit, so that the applied power has not been utilized efficiently for oxygen supplying.

In addition, a method of increasing aeration or inner pressure is also known for improving oxygen supplying, but the method is accompanied by problems that a high pressure affects the metabolism of the fungus bodies and also a large investment is necessary for increasing the capacity of a compressor.

Moreover, equipments for improving oxygen supply by circulating a liquid have come into practical use, such as a fine bubble pump (e.g., JP-A-6-193600 and JP-A-6-330888), a static mixer (e.g., JP-A-5-15753), a fine bubble nozzle (e.g., JP-A-9-201520). However, there are problems that the circulation of a liquid in a culture tank results in insufficient washing in a circulating line which causes bacterial contamination, and a large apparatus is required as the pump for circulation due to a large quantity of circulation in culture of the industrial level. Also, even if the static mixer or nozzle which is placed inside is used, a problem of bacterial contamination due to insufficient washing arises because the mixing part is closed in the line.

Furthermore, in a culture process using a sintered metal element (JP-A-61-56070), when air, oxygen-rich air, or oxygen gas is dispersed and supplied to a culture tank as fine bubbles using a sintered metal element, a large improvement of oxygen supplying ability is observed but there is a problem that solid matter adheres to the membrane during the culture and thus aeration cannot be continued because of increase of pressure loss, even when the aeration is conducted using the sintered metal element instead of the aeration line conventionally employed.

In general, ammonia gas for supplying nitrogen source and for controlling pH is supplied to a culture tank through a diffusing pipe for aeration in a usual aerobic culture for the purpose of efficient dispersion using stirring blades (e.g., Malcolm V. Bartow, *Chemical Engineering*, July, 70 (1999), Daniel I. C. Wang et al., *Fermentation and Enzyme Technology*, 230 (1979), and *Apparatus and Instrument in Bioindustry*, 10, ed. by Joji Takahashi, Japan Bioindustry Association (1987)). From the reason of avoiding bacterial contamination and inhomogeneity of pH and existing a possibility of back flow of a culture liquid at non-working time due to the high solubility of ammonia gas, it is rare to supply ammonia gas alone through a pipe other than a diffusing pipe for aeration. However, when aerobic culture is conducted with the change of the diffusing pipe employed in a conventional process for aerobic culture into a sintered metal element and ammonia is supplied, the present inventors have found for the first time that there arises a problem that solid matter adheres due to the roughness of the membrane surface and pressure loss at aeration increases, whereby it becomes impossible to continue the aeration under the discharge pressure of a current compressor and the use of the membrane should be stopped in the middle of the culture.

SUMMARY OF THE INVENTION

Accordingly, an object of the present invention is to develop a culture apparatus and culture process capable of improving an oxygen supplying rate by 60% or more and supplying ammonia simultaneously and also capable of conducting culture without problems of the membrane occlusion and bacterial contamination, by equipping a current aerating stirrier with a sintered metal membrane as a diffusing pipe.

This and other objects of the present invention have been accomplished by a process for aerobic culture wherein ammonia and oxygen are simultaneously supplied, which comprises: dispersing and supplying air, oxygen, or a mixed gas thereof into a culture tank through a sintered metal membrane attached to the end of a diffusing pipe, and simultaneously, dispersing and supplying ammonia or a mixed gas of ammonia and air into the culture tank through a diffusing pipe other than the above diffusing pipe.

DETAILED DESCRIPTION OF THE INVENTION

Figure 1:
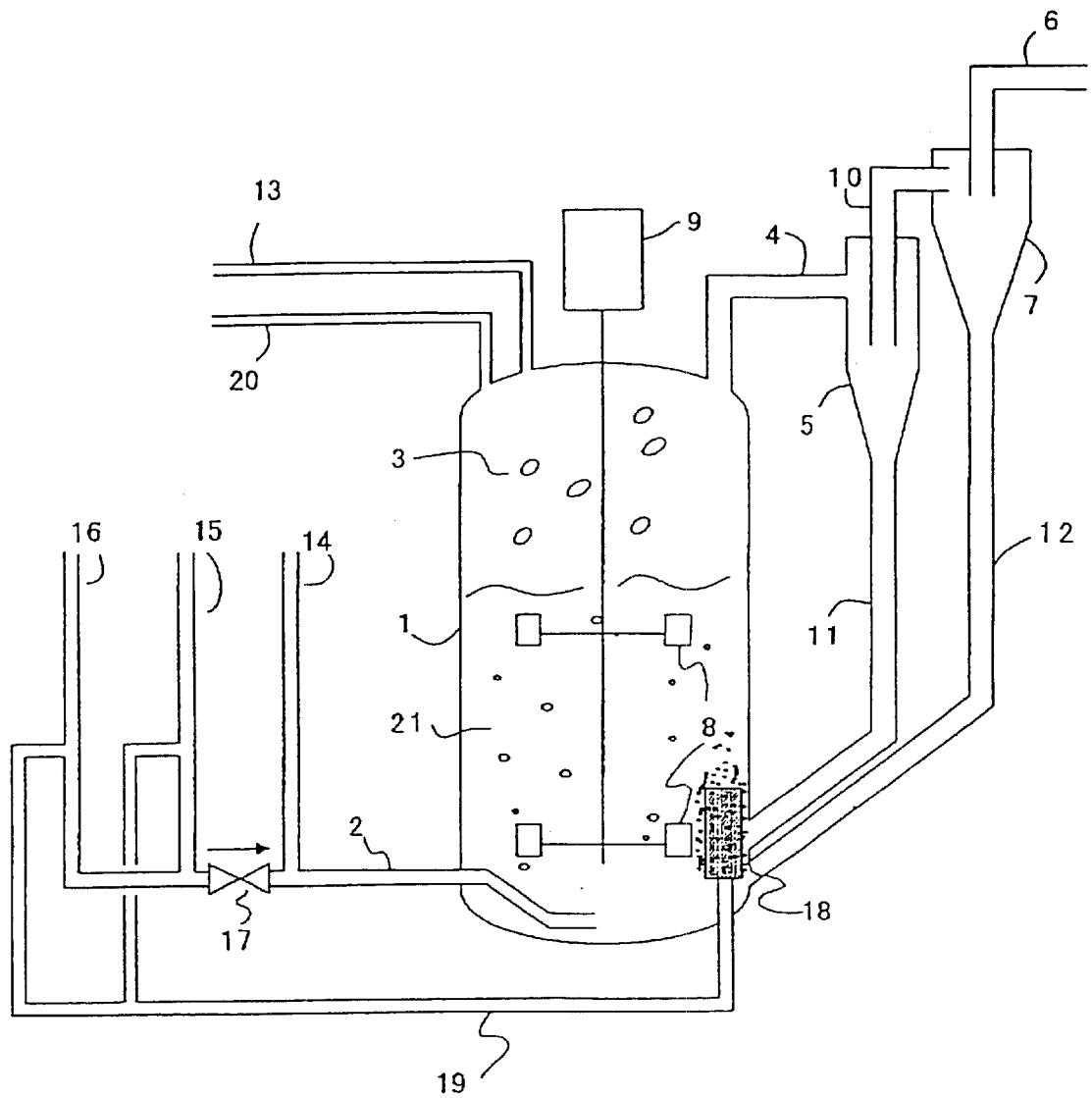
FIG. 1 is a drawing showing the culture apparatus of the present invention.

As a result of extensive studies on the cause for the membrane occlusion, the present inventors have found that the adherence of solid matter to outer surface of the membrane resulted by supplying ammonia causes the occlusion of the sintered metal membrane.

In order to continue a culture under high oxygen supply using a sintered metal membrane, the occlusion of the sintered metal membrane is avoided by supplying ammonia through another diffusing pipe other than the diffusing pipe for supplying oxygen or air. Thus, the present inventors have accomplished the present invention.

More preferably, for preventing the back flow of ammonia gas at non-working time, the present invention relates to a process for aerobic culture, wherein a minute amount of air is continuously supplied through the diffusing pipe.

The aerobic culture in the present invention includes amino acid fermentation, nucleic acid fermentation, yeast fermentation, and mold fermentation. Examples of the amino acid fermentation include glutamic acid fermentation, lysine fermentation, arginine fermentation, and the like. Examples of the nucleic acid fermentation include inosine fermentation, guanosine fermentation, and the like. Moreover, the culture may be conducted under conditions according to the usual manner.

The fungus bodies to be cultured are not particularly limited, so long as they grow in aerobic conditions. Examples include bacteria, yeasts, cells and the like.

For effectively dispersing ammonia supplied into a culture tank, it is preferable to supply ammonia gas from the under part of lower blades having a large shear force. The aeration amount of air supplied through a sintered metal membrane varies depending on the oxygen amount required, but is preferably 10 to 80% of the total aeration amount. The remainder of air is supplied through the conventional diffusing pipe together with ammonia. One example is shown in Table 1.

TABLE 1

|  | Conventional | Membrane |
| --- | --- | --- |
| Aeration amount ($Nm^3$/min) | 25 | 85 |
| Ammonia amount ($Nm^3$/min) | 5 | 0 |

The sintered metal membrane employed in the present invention has a porous structure, and is manufactured by shaping a metal powder having a uniform particle size distribution under pressure and sintering it. The method of manufacturing the sintered metal membrane is not particularly limited, and conditions in the method are easily selected by one of ordinary skill in the usual manner. For example, metal powders are pressurized in a pressure tank over 6,000 kg/cm$^2$G, then sintered in vacuum sintering furnace at 1,200° C. and $10^{-3}$ Torr. The sintered metal membrane is more excellent in thermal resistance and strength than a polymer membrane and a ceramic membrane, so that it is widely employed as a filter in petroleum refining and chemical industry.

The material of the sintered metal membrane to be employed in the present invention may be selected from nickel, stainless steel, inconel, titanium, and the like. There is observed no difference in oxygen supplying ability among the metal materials. Preferred is a membrane made of stainless steel in view of mechanical strength, chemical resistance, thermal shock resistance, and cost.

The form of the sintered metal membrane is not particularly limited, and may be a two-dimensional structure or a three-dimensional structure. Examples of the form include platy, curved, spherical, cylinder-like, conic, cubic, polyhedral forms and the like.

The thickness of the sintered metal membrane is not particularly limited, so long as air, oxygen or a mixed gas thereof can penetrate the sintered metal membrane. Membrane thickness of 1.0 to 10 mm is normally used in combination of membrane strength and of pressure drop by aeration.

The pore size of the sintered metal membrane and the linear velocity of aeration are preferably from 1 to 20 μm and from 0.04 to 0.11 m/s (15 to 400 m/Hr), respectively, as those of a fine bubble-type aerator (JP-A-61-56070, etc.), and more preferably about 5 μm and about 0.04 m/s, respectively.

Air is usually employed as the gas to be employed for aerobic culture, but when a higher oxygen supplying ability is required, oxygen-enriched air, pure oxygen, or the like may be employed by means of an oxygen-generating apparatus or the like.

FIG. 1 shows a culture apparatus in which a membrane is placed, as one example of the culture apparatus for conducting a highly oxygen-requiring culture of aerobic culture using a sintered metal membrane to be employed in the present invention. FIG. 1 will be explained below.

FIG. 1 is a longitudinal sectional view of the culture apparatus at conducting the following example. A culture tank 1 is charged with a culture liquid 21, and a conventional air-supplying pipe 2 for diffusing pipe is placed at the lower part. On the other hand, a gas-discharging pipe 4 for discharging bubbles 3 formed in the culture tank 1 is placed at the upper part. Ammonia for controlling pH is supplied through a pipe 14. For preventing the back flow of ammonia, a back-flow stopping valve 17 is placed between the pipe 14 for ammonia and a pipe 19 connected with a sintered metal membrane 18. The place for providing the sintered metal membrane 18 is desirably a place where the membrane completely sinks in a liquid and which is as low as possible. Through a pipe 15, compressed air is supplied to the conventional diffusing pipe 2 and the diffusing pipe 19 connected with the sintered membrane. A steam pipe 16 for sterilization is connected with the conventional diffusing pipe 2 and the diffusing pipe 19 of the sintered metal membrane. The gas-discharging pipe 4 is connected with a cyclone 5 and the cyclone 5 is connected with the culture tank via a liquid-recycling pipe 11. Moreover, a gas-discharging pipe 10 is connected with a cyclone 7 and the cyclone 7 is connected with the culture tank via a recycling pipe 12. By the way, the liquid-recycling pipe 11 may be, of course, connected with the recycling pipe 12. 6 is a gas-discharging pipe, 8 is stirring blades, 9 is a stirring motor, 13 is an antifoam-adding pipe, and 20 is an adding saccharide-supplying pipe.

The air introduced from the lower part of the culture tank 1 is sheared with the stirring blades and is dispersed into fine bubbles. On the other hand, the air supplied from the sintered metal membrane is supplied to the culture liquid in a finely dispersed state. During the culture, the pH is controlled by supplying ammonia through the conventional gas-inlet line and shearing the gas with stirring blades when the pH is lowered by the metabolism of fungus bodies or the formation of an amino acid or the like.

An oxygen demand by fungus bodies can be satisfied and the culture can be operated without the problem of bacterial contamination by supplying oxygen by means of the culture apparatus of the present invention. Also, productivity of a useful ingredient can be remarkably improved by culturing at a high fungus body concentration.

According to the present invention, productivity can be largely improved without decreasing yields in a culture tank for actual production. The culture can be operated with shortened culture period without the occurrence of bacterial contamination. Thus, there are brought advantages that the production of a target substance per unit of time can be increased and thus productivity can be improved.

The present invention will be specifically explained based on Example.

EXAMPLE 1

A fermentation of glutamic acid was conducted using a glutamic acid-producing fungus, *Brevibacterium lactofer-* mentum ATCC 13869, by a culture apparatus (total volume of the culture tank: 310 kL) shown in FIG. 1. A culture medium was prepared by adding additives to 140 kL of molasses having a saccharide concentration of 80 g/L so as to attain the composition shown in Table 2. About 10 kL of Brevibacterium lactofermentum ATCC 13869 which had been cultured in the medium having the same composition beforehand was inoculated thereto, followed by culturing at 31.5° C. under aeration with stirring while maintaining the pH at 7.5 by ammonia gas. The inner pressure of the culture tank was set at 0.5 kgf/cm$^2$G. When the saccharide concentration in the medium was lowered to less than 3% during the culture, the culture was continued while the saccharide concentration was controlled to from 2 to 4% by adding small portions of molasses having a saccharide concentration of 350 g/L. When the concentration of dissolved oxygen in the medium was lowered to less than 1.6 ppm, the addition of the saccharide was stopped and the concentration of dissolved oxygen was controlled so that the concentration was maintained at 1.6 ppm or more. Moreover, at the time when the fungus quantity reached a predetermined level during the culture, a surfactant, Tween 60, was added to the medium so as to attain the concentration of 0.6% in the medium. As an antifoaming agent, PPG type (polypropylene glycol AZ20R manufactured by Nippon Oil & Fats Co., Ltd.) was employed.

TABLE 2

| Potassium dihydrogenphosphate | 3 g/L |
|---|---|
| Urea | 4 g/L |
| Magnesium sulfate heptahydrate | 0.5 g/L |
| Iron(II) sulfate heptahydrate | 20 mg/L |
| Manganese sulfate tetrahydrate | 20 mg/L |
| Thiamine hydrochloride | 200 μg/L |
| Soybean protein hydrolyzate (total nitrogen content: 40 g/L) | 5 mL/L |
| Biotin | 30 μg/L |

The culture was conducted by means of a culture apparatus to which a sintered metal membrane made of SUS 316L was attached. A sintered metal membrane of 5 μm pore size was used and its surface area was set to keep linear velocity of supplied air 0.04 m/s. The aeration distribution was controlled by a control valve so as to attain the ratio of a conventional line:a sintered metal membrane line=2:8. The oxygen demand by fungus bodies increased immediately after the start of the culture, and 5 hours after the start, the concentration of dissolved oxygen decreased rapidly. Along to the decrease, ammonia for pH control was supplied through the conventional line. After about 10 hours, the saccharide initially added was consumed and the saccharide concentration was lowered to 3% or less, so that the addition of saccharide was started. After about 12 hours, oxygen consumption by fungus bodies reached a maximum value and then a tendency of gradual decrease thereof was observed. After 24 hours of the culture, the culture was terminated when the quantity of the culture liquid reached 76 to 80% of the volume of the culture tank. During the culture, the rate of adding the saccharide did not come up with the consumption, and thus the concentration of dissolved oxygen always showed 3 ppm or more. The final quantity of the culture liquid reached to 240 kL and 86 g/L of glutamic acid was obtained. During the culture, a phenomenon of foaming out of the system was observed but the foaming could be suppressed by a conventional defoaming method, so that the culture could be operated without flowing of the culture liquid out of the cyclone placed at the discharging outlet of the culture tank. Furthermore, it is unnecessary to shear the supplied gas by stirring blades and therefore, the culture could be operated at about 60% of the stirring power required for the conventional method.

Comparative Example 1

Figure 2:
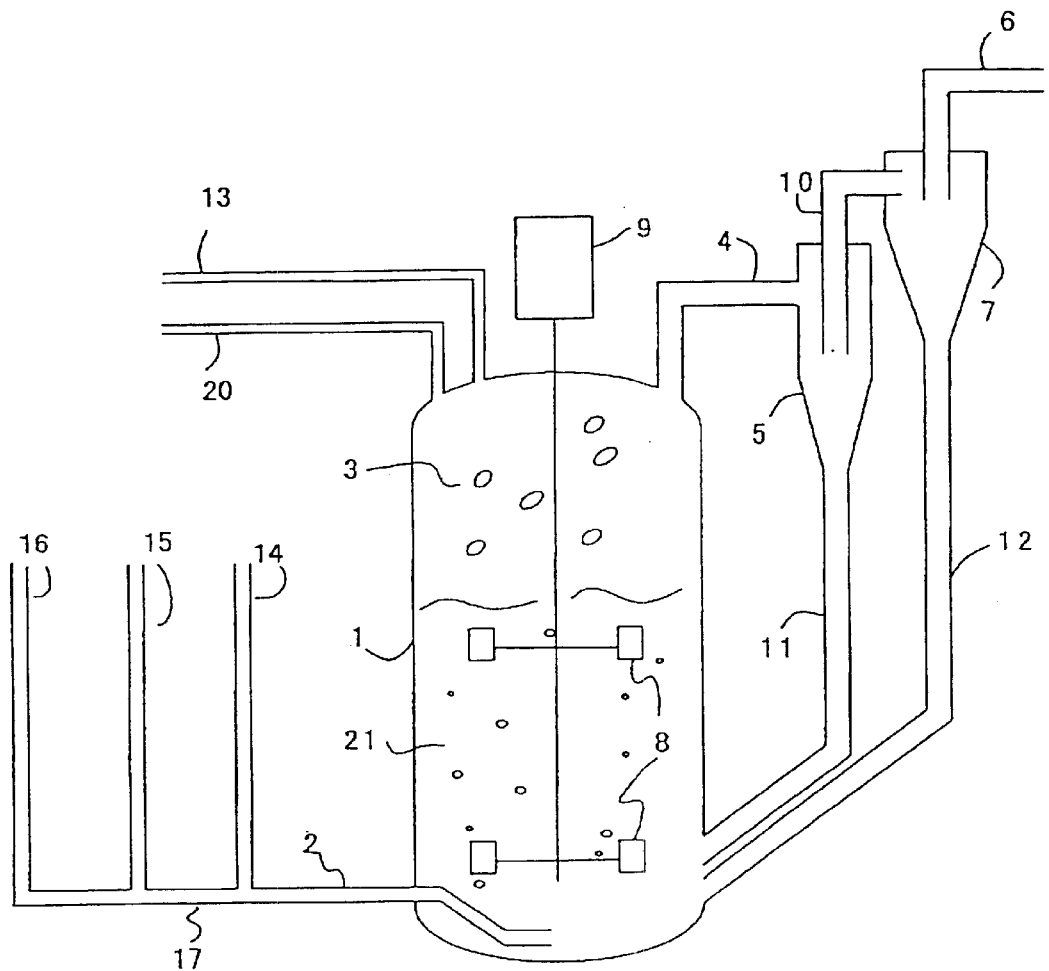
FIG. 2 is a drawing showing the culture apparatus used in Comparative Example 1.

For the purpose of the comparison with Example 1, a culture was conducted by means of a culture apparatus fitted with no sintered metal membrane as shown in FIG. 2. All aeration was conducted through the conventional line. The culture of Brevibacterium lactofermentum ATCC 13869 was conducted under the same culture conditions as those in Example 1 with the same concentration of molasses. As in Example 1, about 5 hours after the start of the culture, dissolved oxygen rapidly decreased. After 10 hours of the culture, the addition of the saccharide was started. For controlling the concentration of dissolved oxygen at 1.6 ppm, the adding rate of the saccharide was lower than the rate in Example 1. After about 12 hours, oxygen demand reached a maximum value but the value was 60% of the value in Example 1. After 40 hours of the culture, the culture was terminated when the quantity of the culture liquid reached 78% of the volume of the culture tank. The final quantity of the culture liquid reached to 240 kL and 84 g/L of glutamic acid was obtained.

Table 3 shows summary of the results obtained in Example 1 and Comparative Example 1.

TABLE 3

| Items to be compared | Comparative Example 1 | Example 1 |
|---|---|---|
| Final quantity of culture liquid (kL) | 242 | 242 |
| Final quantity of culture liquid (%) | 78 | 78 |
| Total volume of culture tank (kL) | 310 | 310 |
| Accumulated concentration of L-glutamic acid (g/L) | 84 | 86 |
| Culture period (hour) | 40 | 26 |
| Productivity (g/L/hour) | 2.1 | 3.3 |
| Oxygen absorbing rate (the rate in Comparative Example = 1) | 1.0 | 1.67 |
| Used power (the power in Comparative Example = 1) | 1.0 | 0.61 |
| Yield (%) | 46.0 | 47.1 |

This application is based on Japanese application No. 2000-396200 filed on Dec. 26, 2000, the entire content of which is incorporated hereinto by reference.

While the invention has been described in detail and with reference to specific embodiments thereof, it will be apparent to one skill in the art that various changes and modifications can be made therein without departing from the spirit and scope thereof. All references cited herein are incorporated in their entirety.

What is claimed is:

1. A process for aerobic culture in which ammonia and oxygen are simultaneously supplied, comprising:
   dispersing and supplying air, oxygen, or a mixed gas thereof into a culture tank through a sintered metal membrane attached the end of a diffusing pipe, and simultaneously,
   dispersing and supplying ammonia or a mixed gas of ammonia and air into the culture tank through a diffusing pipe other than the above diffusing pipe.

2. The process according to claim 1, wherein a sintered metal membrane is a sintered membrane of metals selected from the group consisting of nickel, stainless steel, inconel, and titanium.

* * * * *

UNITED STATES PATENT AND TRADEMARK OFFICE
CERTIFICATE OF CORRECTION

PATENT NO. : 6,534,305 B2
DATED : March 18, 2003
INVENTOR(S) : Okada et al.

It is certified that error appears in the above-identified patent and that said Letters Patent is hereby corrected as shown below:

<u>Title page,</u>
Item [75], Inventors, should read:

-- [75] Inventors: Atsushi Okada, Kanagawa (JP);
Yoshitaka Teratani, Kanagawa (JP);
Naohiro Kadota, Kanagawa (JP);
Hisao Itoh, Kanagawa (JP); Kazuhiro Satoh, Kanagawa (JP) --

Signed and Sealed this

Twenty-second Day of July, 2003

JAMES E. ROGAN
*Director of the United States Patent and Trademark Office*